US012583942B2

(12) United States Patent
Hu et al.

(10) Patent No.: US 12,583,942 B2
(45) Date of Patent: Mar. 24, 2026

(54) ANTI-TETRODOTOXIN ANTIBODY K548, AND PREPARATION METHOD AND USE THEREOF

(71) Applicant: Naval Medical University, Shanghai (CN)

(72) Inventors: Shi Hu, Shanghai (CN); Changhai Lei, Shanghai (CN); Wenyan Fu, Shanghai (CN)

(73) Assignee: Naval Medical University, Shanghai (CN)

( * ) Notice: Subject to any disclaimer, the term of this patent is extended or adjusted under 35 U.S.C. 154(b) by 683 days.

(21) Appl. No.: 18/068,527

(22) Filed: Dec. 20, 2022

(65) Prior Publication Data

US 2023/0279148 A1    Sep. 7, 2023

(30) Foreign Application Priority Data

Dec. 24, 2021    (CN) .......................... 202111600231.2

(51) Int. Cl.
| | |
|---|---|
| *C07K 16/44* | (2006.01) |
| *A61K 9/00* | (2006.01) |
| *A61K 39/00* | (2006.01) |
| *A61K 45/06* | (2006.01) |
| *A61P 39/02* | (2006.01) |
| *C12N 15/63* | (2006.01) |

(52) U.S. Cl.
CPC ............ *C07K 16/44* (2013.01); *A61K 9/0019* (2013.01); *A61K 39/00* (2013.01); *A61K 45/06* (2013.01); *A61P 39/02* (2018.01); *C12N 15/63* (2013.01)

(58) Field of Classification Search
None
See application file for complete search history.

(56) References Cited

U.S. PATENT DOCUMENTS

| | | | |
|---|---|---|---|
| 10,323,100 B1 | 6/2019 | Xu et al. | |
| 10,808,041 B2 | 10/2020 | Kuang et al. | |
| 11,034,774 B2 | 6/2021 | Wells et al. | |

*Primary Examiner* — Daniel C Gamett

(57) ABSTRACT

The present disclosure relates to the technical field of biomedicine, and provides an anti-tetrodotoxin humanized antibody and use thereof. The humanized antibody has a heavy-chain variable region and a light-chain variable region with amino acid sequences shown in SEQ ID NO: 1 to SEQ ID NO: 2, respectively. Affinity analysis shows that the antibody of the present disclosure has prominent affinity. It is proved by experiments that, after mice in an antibody protection group pre-injected with the antibody of the present disclosure are injected with tetrodotoxin, no mice shows toxic symptoms, and during continuous observation for one month, no toxic lethality occurs, indicating that the antibody of the present disclosure shows excellent anti-tetrodotoxin effects, excellent preventive or therapeutic effects on puffer fish-related biological injuries, and promising clinical application prospects.

8 Claims, No Drawings

Specification includes a Sequence Listing.

ANTI-TETRODOTOXIN ANTIBODY K548, AND PREPARATION METHOD AND USE THEREOF

CROSS REFERENCE TO RELATED APPLICATION

This application claims priority to the Chinese Patent Application No. 202111600231.2 with a filing date of Dec. 24, 2021. The content of the aforementioned application, including any intervening amendments thereto, is incorporated herein by reference.

CROSS-REFERENCE TO A SEQUENCE LISTING

This application includes a Sequence Listing submitted electronically as a text file named 0501SEQ list.xml, created on May 30, 2023, with a size of 3,102 bytes. The Sequence Listing is incorporated by reference herein.

TECHNICAL FIELD

The present disclosure belongs to the technical field of biomedicine, and specifically relates to an anti-tetrodotoxin humanized antibody K548, a preparation method and use thereof in the preparation of tetrodotoxin formulations.

BACKGROUND

The puffer meat is tender and delicious. The fish skin with thorns has a thick and gelatinous texture, which is sticky and tastes far better than shark fins and sea cucumbers. Therefore, puffer fish is known as the first of the "Three Fresh Dishes on the Yangtze River". However, most puffer fish contain tetrodotoxin (TTX) concentrated in the ovary, liver, kidney, blood, eyes, gills, and skin. Tetrodotoxin is relatively stable, and is not easy to be eliminated by salting, sun exposure, and general heating and cooking.

The chemical research of tetrodotoxin began in 1909. After 1964, Woodward determined the structure of TTX. In 1972, Kishi et al. successfully synthesized tetrodotoxin by chemical methods. Tetrodotoxin has a molecular formula of $C_{11}H_{17}N_3O_8$ and a molecular weight of 319.27; the tetrodotoxin molecule is mainly composed of three nitrogen atoms, which form a special structure with the hydrogen and oxygen atoms. The tetrodotoxin molecule includes one carbocyclic ring, one guanidino group, six hydroxyl groups, and a separate ring ligated by semi-aldose lactone at the C-5 and C-10 positions. Tetrodotoxin is also one of the deadliest poisons in the world, and is called by some experts "one of nature's strangest molecules". 1 g of tetrodotoxin is 10,000 times more toxic than 1 g of cyanide.

In order to detoxify tetrodotoxin, scientists have tested a variety of methods, including antibodies as one of the effective manners. Because antibodies can efficiently and specifically bind to various antigen proteins in vivo and in vitro, antibodies can not only be used to regulate the functions of immune systems, but also can be used for various detection methods with high sensitivity. At present, antibody drugs are the most important part of biotechnology drugs, and antibody reagents are also one of the most common reagents used in medical diagnosis and biological research. Therefore, antibody-related biological products have extremely-promising application prospects and extremely-high commercial values. Antibodies can be obtained in a variety of ways. For toxin proteins, antibodies are highly neutralizing as a potential antitoxin drug.

SUMMARY

The present disclosure is intended to study an anti-tetrodotoxin antibody K548, and a preparation method and use thereof based on the above research background, that is, to provide a brand-new humanized antibody, and a preparation method and use thereof.

In a first aspect of the present disclosure, an anti-tetrodotoxin humanized antibody K548 is provided, where the heavy-chain variable region of the antibody K548 is composed of an FRH1-CDRH1-FRH2-CDRH2-FRH3-CDRH3-FRH4 region; and the light-chain variable region of the antibody K548 is composed of an FRL1-CDRL1-FRL2-CDRL2-FRL3-CDRL3-FRL4 region. The heavy-chain variable region and the light-chain variable region have amino acid sequences shown in SEQ ID NO: 1 and SEQ ID NO: 2, respectively.

The heavy-chain variable region has the amino acid sequence (SEQ ID NO: 1) as follows:

EVQLVESGGGLYKHLIYDDPGRSLRLSCAASGFTFDDYAMHWVRQAPGK

GLEWVSAIFWTISHNWGRFTISRDNAKNSLYLQMNSLRAEDTAVYYCAK

VKFSKFVMLDYWGQGTLVTVSS

The light-chain variable region has the amino acid sequence (SEQ ID NO: 2) as follows:

DIQMTQSPSSLSASVGDRVTITCRANTNGLCDPQDNWYQQKPGKAPKLL

IYAYRCWNWSGVPSRFSGSGSGTDFTLTISSLQPEDVATYYCQWPYGMY

NKRPFGQGTKVEIK

The humanized antibody can be obtained as follows: a humanized antibody phage display library is first constructed, then the humanized antibody is screened, specific positive clones are screened by phage enzyme-linked immunosorbent assay (ELISA), and after sequence analysis, the humanized antibody is obtained. After expressing and purifying the humanized antibody in a 293 system, high-purity humanized antibodies are obtained.

In a second aspect of the present disclosure, a preparation method of the humanized antibody is provided, including the following steps:

(A) synthesizing a full-length humanized antibody based on a whole genome of a variable region gene of the antibody K548;

(B) cloning the full-length humanized antibody obtained in step (A) into an expression vector by PCR, and determining a correct clone after sequencing verification; and (C) introducing the expression vector into a host cell for fusion protein expression.

In the present disclosure, any suitable vectors are applicable, which may preferably be pGEM-T, Pet32a, pcDNA3.1, pEE6.4, pEE12.4, pDHFR, or pDR1; and the expression vector may include a fusion DNA sequence ligated with appropriate transcription and translation regulatory sequences.

In the present disclosure, a mammalian or insect host cell or a prokaryotic cell culture system can be used for the expression of the fusion protein of the present disclosure. An available host cell may be a prokaryotic cell with the above-mentioned vector, which can be one from the group consisting of DH5a, Top10, BL21 (DE3), and TG1.

The fusion protein of the present disclosure can be easily produced in the following cells: mammalian cells, such as CHO, NSO, HEK293, BHK, or COS cells; bacterial cells, such as *E. coli, Bacillus subtilis (B. subtilis)*, or *Pseudomonas fluorescens (P. fluorescens)*; and insect cells, or fungal or yeast cells, which are cultivated using techniques known in the art.

The preparation method of the fusion protein disclosed in the present disclosure may include: cultivating the above-mentioned host cell under expression conditions to express, isolate, and purify the fusion protein. With the above method, the antibody can be purified into a substantially homogeneous substance, such as a single band of sodium dodecyl sulphate-polyacrylamide gel electrophoresis (SDS-PAGE).

The fusion protein disclosed in the present disclosure can be isolated and purified by affinity chromatography. According to characteristics of an affinity column used, a conventional method such as high-salt buffer and pH change can be used to elute the fusion protein peptide bound to the affinity column.

Various protein purification methods can be used, and such methods are known in the art and described in, for example, (Wilchek and Bayer, 1990, Methods in enzymology) (Scopes, 2013, Protein purification: principles and practice).

According to Biacore analysis, the humanized antibody of the present disclosure has prominent affinity, and small animal experiments have shown that, after mice in a protection group pre-injected with the humanized antibody of the present disclosure are injected with tetrodotoxin, no mice shows neurotoxic symptoms, and during continuous observation for one month, no toxic lethality occurs. It indicates that the humanized antibody of the present disclosure has an excellent anti-tetrodotoxin effect.

Therefore, in a third aspect of the present disclosure, a pharmaceutical composition with the humanized antibody is provided. In addition to the humanized antibody, the pharmaceutical composition may include a pharmaceutically acceptable drug carrier.

The humanized antibody of the present disclosure and a pharmaceutically acceptable adjuvant together constitute a pharmaceutical formulation composition, thereby exerting a more stable therapeutic effect. The formulation can ensure the conformational integrity of an amino acid core sequence of the humanized antibody disclosed in the present disclosure, and can also protect multifunctional groups of the protein to prevent its degradation (including but not limited to aggregation, deamination, or oxidation).

Normally, a liquid preparation can be stored at 2° C. to 8° C. for at least one year, and a lyophilized formulation can be stored at 30° C. for at least six months. The formulation can be a suspension, an injection, a lyophilized formulation, or the like commonly used in the pharmaceutical field, and preferably an injection or a lyophilized formulation.

For the injection or lyophilized formulation of the humanized antibody disclosed in the present disclosure, the pharmaceutically acceptable adjuvant may include one or a combination of two or more from the group consisting of a surfactant, a solution stabilizer, an isoosmotic adjusting agent, and a buffer. The surfactant may include a non-ionic surfactant, such as polyoxyethylene sorbitan fatty acid esters (Tween 20 or 80); poloxamer (such as poloxamer 188); Triton; sodium dodecyl sulfate (SDS), sodium lauryl sulfate (SLS); myristyl, linoleyl or stearyl sarcosine; Pluronics; and MONAQUAT™; and the surfactant may be added at an amount that minimizes the granulation tendency of the bifunctional bispecific antibody protein. The solution stabilizer can be sugar, including reducing sugar and non-reducing sugar; amino acid, including monosodium glutamate (MSG) or histidine; and alcohols, including one or a combination of two or more from the group consisting of triol, higher sugar alcohol, propylene glycol (PG), and polyethylene glycol (PEG); and the solution stabilizer may be added at an amount that enables a final formulation to remain stable within a period of time considered by those skilled in the art to reach a stable state. The isoosmotic adjusting agent can be one from the group consisting of sodium chloride and mannitol. The buffer can be one from the group consisting of tris(hydroxymethyl)aminomethane (TRIS), a histidine buffer, and a phosphate buffer.

The above-mentioned formulation is a composition including the humanized antibody, and after being administered to animals including humans, the formulation shows a prominent anti-tetrodotoxin effect. Specifically, the formulation is effective in preventing and/or treating tetrodotoxin poisoning, and can be used as an anti-tetrodotoxin drug.

In the present disclosure, when the humanized antibody and the composition thereof are administered to animals including humans, a dosage varies with the age and body weight of the patient, the characteristics and severity of the disease, and the route of administration. The total dosage can be defined within a specified range with reference to results of animal experiments and various other conditions. Specifically, a dosage of intravenous injection may be 1 mg/d to 1,800 mg/d.

In a fourth aspect of the present disclosure, use of the humanized antibody (specifically use in the preparation of an anti-tetrodotoxin formulation drug) for preventing or treating jellyfish stings is provided.

DETAILED DESCRIPTION OF THE EMBODIMENTS

The following examples and experimental examples are provided to further illustrate the present disclosure, and shall be construed as a limitation to the present disclosure. The examples do not include detailed descriptions of traditional methods, such as methods for constructing vectors and plasmids, methods for inserting genes encoding proteins into such vectors and plasmids, or methods for introducing plasmids into host cells. Such methods are well known to those of ordinary skill in the art, and are described in many publications, including Sambrook, J., Fritsch, E. F. and Maniais, T. (1989) Molecular Cloning: A Laboratory Manual, $2^{nd}$ edition, Cold spring Harbor Laboratory Press.

Example 1. Preparation and Expression of a Humanized Antibody

The humanized antibody was derived from a phage-displayed antibody library. The methods for constructing and expressing the antibody were conventional experimental techniques in the field, which were briefly described as follows:

(1) A heavy chain and a light chain of the antibody were synthesized by whole genome, where amino acid sequences of a heavy-chain variable region and a light-chain variable region were shown in SEQ ID NO: 1 and SEQ ID NO: 2, respectively.

(2) Expression and purification of the antibody

The expression and purification of the antibody were conducted according to a method in the literature [Hu S, Fu W, Li T, et al. Antagonism of EGFR and Notch limits resistance to EGFR inhibitors and radiation by decreasing tumor-initiating cell frequency [J]. *Science Translational Medicine,* 2017, 9 (380)], and a purity of the antibody was identified by SDS-PAGE and reached more than 95%.

Example 2. Biacore Analysis

An anti-tetrodotoxin antibody was coated on a CM5M5 chip (GE), and after the antibody to be tested was captured,

TABLE 2

| Test results of the anti-tetrodotoxin effect of the antibody | | | |
|---|---|---|---|
| | Total | Number of survivors on the day | Number of survivors after one month |
| Humanized antibody | 10 | 10 | 10 |
| Control group | 10 | 0 | 0 |

The preferred examples of the present disclosure have been described in detail above, but the present disclosure is not limited to these examples. Those skilled in the art can make various equivalent variations or substitutions without departing from the spirit of the present disclosure, and these equivalent variations or substitutions are all included in the scope defined by the claims of this application.

SEQUENCE LISTING

```
Sequence total quantity: 2
SEQ ID NO: 1            moltype = AA  length = 120
FEATURE                 Location/Qualifiers
source                  1..120
                        mol_type = protein
                        organism = Synthetic construct
SEQUENCE: 1
EVQLVESGGG LYKHLIYDDP GRSLRLSCAA SGFTFDDYAM HWVRQAPGKG LEWVSAIFWT  60
ISHNWGRFTI SRDNAKNSLY LQMNSLRAED TAVYYCAKVK FSKFVMLDYW GQGTLVTVSS  120

SEQ ID NO: 2            moltype = AA  length = 112
FEATURE                 Location/Qualifiers
source                  1..112
                        mol_type = protein
                        organism = Synthetic construct
SEQUENCE: 2
DIQMTQSPSS LSASVGDRVT ITCRANTNGL CDPQDNWYQQ KPGKAPKLLI YAYRCWNWSG  60
VPSRFSGSGS GTDFTLTISS LQPEDVATYY CQWPYGMYNK RPFGQGTKVE IK           112
``` the affinity of each fusion protein was detected by Biacore T100 (GE Healthcare). Specific detected affinity values were shown in Table 1.

TABLE 1

| Biacore analysis results | | |
|---|---|---|
| Parameter | Unit | |
| Binding affinity/kinetics | KD (nM) | 48.6 |

Example 3. Small Animal Experiment

32 C57 mice with a body weight of (20±2) g were selected and fasted for 12 h before the experiment (without water deprivation). The mice were randomly divided into three groups (half female and half male for each group): half-lethal dosage tetrodotoxin group: 12 mice; drug protection group: 10 mice, which were pre-injected with the humanized antibody at 10 mg/kg; and blank control group: 10 mice, which were administered with normal saline. The mice were administered intraperitoneally. Within 1 h after the administration, the mice in the blank control group all showed typical neurotoxic symptoms. None of the mice in the antibody protection group showed neurotoxic symptoms, and during continuous observation for one month, no toxic lethality occurred. Specific results were shown in Table 2.

What is claimed is:

1. An anti-tetrodotoxin humanized antibody K548, comprising a heavy-chain variable region with an amino acid sequence shown in SEQ ID NO: 1, and a light-chain variable region with an amino acid sequence shown in SEQ ID NO: 2.

2. The anti-tetrodotoxin antibody K548 according to claim 1, wherein the heavy-chain variable region comprises FRH1-CDRH1-FRH2-CDRH2-FRH3-CDRH3-FRH4 regions; and the light-chain variable region comprises FRL1-CDRL1-FRL2-CDRL2-FRL3-CDRL3-FRL4 regions.

3. A nucleotide encoding the anti-tetrodotoxin antibody K548 according to claim 1.

4. A preparation method of the anti-tetrodotoxin antibody K548 according to claim 1, comprising the following steps: (A) synthesizing a polynucleotide encoding a full-length humanized antibody based on a whole genome of a variable region gene of the antibody K548; (B) cloning the polynucleotide obtained in step (A) into an expression vector by PCR, and determining a correct clone by sequencing verification; and (C) introducing the expression vector into a host cell for fusion protein expression.

5. The preparation method according to claim 4, wherein the expression vector is pGEM-T, Pet32a, pcDNA3.1, pEE6.4, pEE12.4, pDHFR, or pDR1; the expression vector comprises a fusion DNA sequence ligated with appropriate transcription and translation regulatory sequences; and the host cell is a prokaryotic cell, a mammalian cell, a bacterial cell, an insect cell, or a fungal cell.

6. A pharmaceutical composition comprising the anti-tetrodotoxin antibody K548 according to claim 1, wherein the pharmaceutical composition further comprises a pharmaceutically acceptable drug carrier.

7. The pharmaceutical composition according to claim 6, wherein the pharmaceutical composition is an injection or a lyophilized formulation; and the pharmaceutically acceptable drug carrier comprises one or a combination of two or more from the group consisting of a surfactant, a solution stabilizer, an isoosmotic adjusting agent, and a buffer.

8. The pharmaceutical composition according to claim 6, wherein the injection or the lyophilized formulation is intravenously injected at a dosage of 1 mg/d to 1,800 mg/d.

* * * * *